United States Patent [19]

Yanaihara et al.

[11] 4,330,466

[45] May 18, 1982

[54] PROCESS FOR THE PRODUCTION OF CHOLECYSTOKININ-PANCREOZYMIN C-TERMINAL PEPTIDE AMIDE SULFATE ESTERS

[75] Inventors: Noboru Yanaihara, Shizuoka; Nobuo Sugiura, Hajima, both of Japan

[73] Assignee: Amano Pharmaceutical Co., Ltd., Nagoya, Japan

[21] Appl. No.: 217,187

[22] Filed: Dec. 16, 1980

[30] Foreign Application Priority Data

Jun. 10, 1980 [JP] Japan .................................. 55-78227

[51] Int. Cl.³ ........................................... C07C 103/52
[52] U.S. Cl. ............................................ 260/112.5 R
[58] Field of Search .................. 260/112.5 R; 424/177

[56] References Cited

U.S. PATENT DOCUMENTS

| | | | |
|---|---|---|---|
| 3,579,494 | 5/1971 | Ondetti et al. | 260/112.5 |
| 3,723,406 | 3/1973 | Ondetti et al. | 260/112.5 |
| 3,892,726 | 7/1975 | Ondetti et al. | 260/112.5 |
| 3,937,819 | 2/1976 | Ondetti et al. | 424/177 |
| 4,102,878 | 7/1978 | Penke et al. | 260/112.5 R |

*Primary Examiner*—Delbert R. Phillips
*Attorney, Agent, or Firm*—Oblon, Fisher, Spivak, McClelland & Maier

[57] ABSTRACT

A novel process for the production of cholecystokinin-pancreozymin C-terminal peptide amide sulfate esters in a high yield and through a simple operation is described. A protected peptide amide is reacted with sulfur trioxide-pyridine complex and resulting protected piptide amide sulfate ester is then isolated in the form of its calcium salt. Thereafter, the protecting groups and calcium are removed. Sulfuric acid resulting from unreacted sulfur trioxide-pyridine complex may be precipitated and easily removed in the form of calcium sulfate.

8 Claims, No Drawings

PROCESS FOR THE PRODUCTION OF CHOLECYSTOKININ-PANCREOZYMIN C-TERMINAL PEPTIDE AMIDE SULFATE ESTERS

BACKGROUND OF THE INVENTION

1. Field of the Invention

The present invention relates to a novel process for the production of a cholecystokinin-pancreozymin C-terminal peptide amide sulfate ester of the formula (I)

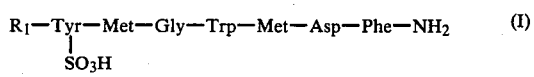

where $R_1$ represents Asp— or Asp—Arg—Asp—.

2. Description of the Prior Art

Cholecystokinin-pancreozymin (hereinafter referred to simply as CCK) is a gastrointestinal peptide hormone consisting of 33 amino acid residues, and has the gallbladder contraction and pancreatic secretion effects, thus playing an important role in the digestive and absorption system.

Further, it has been found that such effects of CCK are derived from its C-terminal octapeptide amide sulfate ester and that cholecystokinin-pancreozymin C-terminal octapeptide amide sulfate ester (in the formula (I), $R_1$=Asp—) (hereinafter referred to as CCK-8) has a stronger activity than the natural CCK. Thus, various studies have been made to synthesize the CCK-8 and its homologues such as cholecystokinin-pancreozymin C-terminal decapeptide amide sulfate ester (in the formula (I), $R_1$=Asp—Arg—Asp—) (hereinafter referred to as CCK-10).

For the production of the compound of the formula (I), there has been known (1) a method wherein free octapeptide amide is reacted with concentrated sulfuric acid or a mixture of sulfuric acid and potassium hydrogensulfate at a lower temperature (U.S. Pat. No. 3,705,140), or (2) a method wherein a protected peptide amide of the formula (II)

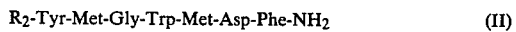

where $R_2$ is

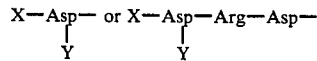

wherein X is an amino protecting group and Y is absence or a carboxyl protecting group, is reacted with sulfur trioxide-pyridine complex to form a sulfate ester and then the protecting groups are removed [J.Am.-Chem.Soc. 92, 195 to 199 (1970)].

In these methods, the sulfate esterified reaction solution is poured into a cold ethanol for precipitation and the precipitates are dissolved in an ammonium carbonate solution and refined by means of e.g. DEAE-Sephadex thereby to obtain the intended product. However, the compound of the formula (I) is extremely unstable, and the decomposition is likely to occur during the post-treatment, which leads to reduction of yield and activity. The yield is 10% according to the method (1) and 30% according to the method (2), thus presenting extremely low yield in either case.

SUMMARY OF THE INVENTION

Under these circumstances, the present inventors have conducted an extensive research to overcome the above drawbacks, and as a result, have found that it is possible to stabilize the protected peptide amide sulfate ester by converting it into a calcium salt form, and that it is possible to obtain the compound of the formua (I) in good yield with a simple operation by removing unreacted sulfur trioxide-pyridine complex in the form of the calcium salt precipitate of sulfuric acid resulting from the unreacted complex. The present invention has been accomplished by these discoveries.

Namely, the present invention provides a process for the production of a cholecystokinin-pancreozymin C-terminal peptide amide sulfate ester of the formula (I) which comprises reacting the protected peptide amide of the formula (II) with a sulfur trioxide-pyridine complex, isolating the protected peptide amide sulfate ester thereby obtained, in the form of a calcium salt, and then removing the protecting group or groups and desalting the resulting non-protected calcium salt.

DESCRIPTION OF THE INVENTION

The amino protecting group represented by X and the carboxyl protecting group represented by Y in the starting material (II) of the present invention, may be any of appropriate ones, for instance an amino protecting group such as tert-butyloxycarbonyl, benzoxycarbonyl, or α, α-dimethyl-3,5-dimethoxybenzyloxycarbonyl, and a carboxyl protecting group such as tert-butyl, or benzyl.

The protected peptide amide as the starting material, may be prepared by a known method in which amino acid components may be combined in an optional order.

In carrying out the present invention, firstly the protected peptide amide is sulfate esterified with sulfur trioxide-pyridine complex. This reaction is per se already known and may, for instance, be carried out by a method wherein the protected peptide amide is dissolved in an inert solvent such as dimethylformamide or pyridine, and sulfur trioxide-pyridine complex in an amount of about 10 times as much is added thereto for reaction. The reaction is preferably carried out at a low temperature at first and then at room temperature for about 20 hours.

Then, the solvent is removed by evaporation from the reaction solution, and added to the residue are a solvent such as methanol, butanol, ethanol, or dimethylformamide, and an aqueous solution of a water soluble calcium salt, and as a result the protected peptide amide sulfate ester is converted to calcium salt thereof. As a water soluble calcium salt, there may be mentioned a salt of an organic acid such as calcium acetate or calcium propionate, and a salt of an inorganic acid such as calcium chloride, calcium bromide or calcium nitrate. An organic or inorganic salt of calcium is preferably used since it is reacted with sulfuric acid resulting from the unreacted sulfur trioxide-pyridine complex to form a water insoluble calcium sulfate which can be removed as precipitate.

Further, if this solution is refined by chromatography on a column of e.g. Sephadex LH-20, it is possible to obtain the calcium salt of the protected peptide amide sulfate ester in a yield of 95% or more.

Then, the removal of the protecting group or groups and desalting, are carried out. The removal of the protecting group or groups may be conducted by a conventional method, for instance by a treatment with trifluoroacetic acid, trichloroacetic acid, hydrochloride acid-dioxane, formic acid, p-toluene sulfonic acid, or glacial acetic acid-mercaptoethane sulfonic acid. The desalting may easily be carried out by e.g. ion-exchange chromatography or e.g. a column of DEAE-cellulose.

According to the present invention as described above, it is possible to obtain a highly effective CCK-8 or CCK-10 in a good yield and thus the process of the present invention is extremely advantageous as an industrial process.

EXAMPLE 1

(i) Dissolved in a mixed solution of 50 ml of dimethylformamide and 5 ml of pyridine, were 2.44 g (2 mM) of tertbutyloxycarbonyl-β-tert-butyl-L-aspartyl-L-tyrosyl-L-methionyl-glycyl-L-tryptophyl-L-methionyl-L-aspartyl-L-phenylalanine amide, and added thereto on an ice bath, were 3.18 g (20 mM) of sulfur trioxide-pyridine complex. The mixture was stirred on an ice bath for 30 minutes and further at room temperature for 20 hours. The solvent was removed from the reaction solution under a reduced pressure, and added to the residue, were 10 ml of methanol, 10 ml of butanol and 22 ml of a 1 M aqueous solution of calcium acetate. Then, the mixture was neutralized by the addition of a diluted aqueous ammonia solution. Precipitated calcium sulfate was removed by centrifugation, and washed with a small amount of a solution mixture of 1-butanol-methanol-water (2:2:1). The decanted solution and washed solutions were collected and chromatographed on a column of Sephadex LH-20 (3.5×140 cm) wherein the elution was made by a mixed solution of 1-butanol-methanol-water (2:2:1). The fractions containing the desired component were collected, the solvent removed and the residue freeze-dried, whereupon 2.55 g of a calcium salt of protected octapeptide amide sulfate ester was obtained (yield of 95%).

(ii) The calcium salt of protected octapeptide amide sulfate ester obtained as described above, was dissolved by the addition of 10 ml of trifluoroacetic acid containing 0.2 ml of ethanedithiol under an ice cooled condition, and left to stand at room temperature for 40 minutes. Dry ether was added to the reaction solution, and the precipitate was filtered and dried. The dried precipitate was dissolved in a 0.1 M aqueous solution of ammonium carbonate and subjected to ion-exchange chromatography on a column of DEAE-cellulose (Whatman DE-32) (3.0×16 cm). Gradient elution was carried out with use of 0.1 to 0.5 M ammonium carbonate (pH 9.2; 1000 ml each), and the fractions containing the desired component were collected The solvent was removed and freeze-drying was repeated to obtain 1.15 g of CCK-8 (yield of 50.4%).

$[\alpha]_D^{23}: -20.8°$ (c=1.0, 1 N-NH$_4$OH)

IR: 1050 cm$^{-1}$ (sulfate ester)

Elemental analysis: $C_{40}H_{62}N_{10}O_{16}S_3 \cdot 4H_2O$: Calculated values (%): C 48.43, H 5.81, N 11.52. Found (%): C 48.10, H 5.44, N 11.57.

Amino acid analysis based on acid hydrolysis: Aspartic acid 1.97 (2), glycine 0.99 (1), methionine 2.04 (2), tyrosine 1.00 (1), phenylalanine 1.00 (1).

Amino acid analysis based on enzyme digestion: Tryptophan 1.10 (1), tyrosine sulfate 1.01 (1), aspartic acid 1.93 (2), glycine 1.03 (1), methionine 2.08 (2), phenylalanine 1.02 (1).

Biological activity: 48,000 to 50,000 CHRU/mg (gallbladder contraction of guinea pigs).

EXAMPLE 2

(i) Added to a mixed solution of 50 ml of dimethylformamide and 5 ml of pyridine, were 1.49 g (1.0 mM) of tert-butyloxycarbonyl-β-tert-butyl-L-aspartyl-L-arginyl-L-aspartyl-L-tyrosyl-L-methionyl-glycyl-L-tryptophyl-L-methionyl-L-aspartyl-L-phenylalanine amide, and added thereto on an ice bath, was 1.59 g (10 mM) of sulfur trioxide-pyridine complex. The mixture was stirred on an ice bath for 30 minutes and further at room temperature for 20 hours. The solvent was removed from the reaction solution under a reduced pressure, and added to the residue were 12 ml of methanol, 6 ml of 1-butanol and 12 ml of a 1 M aqueous solution of calcium acetate. Then, the mixture was neutralized by the addition of a diluted aqueous ammonia solution. Precipitated calcium sulfate was removed by centrifugation and the decanted solution was chromatographed on a column of Sephadex LH-20 (3.5×140 cm) wherein the elution was made by a mixed solution of 1-butanol-methanol-water (2:1:2). The fractions containing the desired component were collected, the solvent removed and the residue freeze dried, whereupon 1.70 g of calcium salt of protected decapeptide amide sulfate ester was obtained (yield of 100%).

(ii) The calcium salt of protected decapeptide amide sulfate ester obtained as described above, was dissolved by the addition of 10 ml of trifluoroacetic acid containing 0.2 ml of ethanedithiol under an ice cooled condition, and left to stand at room temperature for 40 minutes. Dry ether was added to the reaction solution, and the precipitate was filtered off and dried. The dried precipitate was dissolved in 100 ml of a 0.05 M aqueous solution of ammonium carbonate and subjected to ion-exchange chromatography on a column of DEAE-cellulose. Gradient elution was carried out with use of 0.05 to 0.3 M ammonium carbonate (1,000 ml each), and the fractions containing the desired component were collected. The solvent was removed by evaporation and the freeze drying was repeated to obtain 0.566 g of CCK-10 (yield of 40%).

$[\alpha]_D^{23}: -22.0°$ (c=1.0, 1 N-NH$_4$OH).

IR: 1050 cm$^{-1}$.

Elemental analysis: $D_{59}H_{79}N_{15}O_{20}S_3 \cdot CH_3COOH \cdot 4H_2O$: Calculated values (%): C 47.37, H 5.93, N 13.58. Found (%): C 46.85, H 5.57, N 13.39.

Amino acid analysis based on acid hydrolysis: Arginine 1.01 (1), aspartic acid 3.05 (3), glycine 1.00 (1), methionine 1.97 (2), tyrosine 1.00 (1), phenylalanine 0.98 (1).

Amino acid analysis based on enzyme digestion: Tryptophan 0.81 (1), arginine 1.21 (1), tryrosine sulfate 0.78 (1), aspartic acid 2.81 (3), glycine 0.91 (1), methionine 1.78 (2), phenylalanine 1.27 (1).

Biological activity: 48,000 CHRU/mg.

EXAMPLE 3

(i) Dissolved into a mixed solution of 10 ml of dimethyl-formamide and 1 ml of pyridine, were 116 mg (0.1 mM) of tert-butyloxycarbonyl-L-aspartyl-L-tyrosyl-L-methionylglycyl-L-tryptophyl-L-methionyl-L-aspartyl-L-phenylalanine amide, and added thereto on an ice bath were 159 mg (1 mM) of sulfur trioxide-pyridine complex. The mixture was stirred and allowed to react on an ice bath for 30 minutes and further at room temperature for 20 hours. The solvent was removed by evaporation from the reaction solution under a reduced pressure, and added to the residue were 2 ml of methanol, 2 m of 1-butanol and 1.2 ml of 1 M calcium acetate. The mixture was neutralized with a diluted aqueous ammonia and deposited calcium sulfate was removed by centrifugation. This solution was chromatographed on a column of Sephadex LH-20 (2.5×140 cm) wherein the elution was made with a mixed solution of methanol-1-butanol-water (2:2:1). The fractions containing the desired component were collected and freeze dried to obtain the calcium salt of protected octapeptide amide sulfate ester (yield of 90%).

(ii) The calcium salt of protected octapeptide amide sulfate ester obtained as described above, was treated with 0.5 ml of trifluoroacetic acid containing 0.01 ml of ethandithiol at room temperature for 20 minutes. Dry ether was added to the reaction solution, and resulted precipitate was filtered off and dried. The dried precipitate was dissolved in a 0.1 M aqueous solution of ammonium carbonate and subjected to ion-exchange chromatography on a column of DEAE-cellulose (1.2×6 cm). Gradient elution was carried out with use of 0.1 to 0.5 M ammonium carbonate (pH 9.2; 300 ml each), and the active fractions were collected. The solvent was removed and freeze-drying was repeated to obtain 57.4 mg of CCK-8 (yield of 50.2%).

What is claimed is:

1. A process for the production of a cholecystokinin-pancreozymin C-terminal peptide amide sulfate ester of the formula (I),

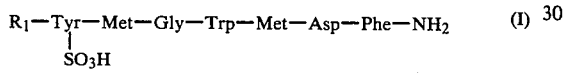

$$R_1-Tyr-Met-Gly-Trp-Met-Asp-Phe-NH_2 \quad (I)$$
$$\phantom{R_1-Tyr-}|$$
$$\phantom{R_1-Ty}SO_3H$$

where $R_1$ represents Asp— or Asp—Arg—Asp—, which comprises:

(1) reacting a protected peptide amide of the formula (II),

$$R_2\text{-Tyr-Met-Gly-Trp-Met-Asp-Phe-NH}_2 \quad (II)$$

where $R_2$ represents

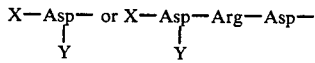

$$X-\underset{\underset{Y}{|}}{Asp}- \text{ or } X-\underset{\underset{Y}{|}}{Asp}-Arg-Asp-$$

wherein X is an amino protecting group and Y is a carboxyl protecting group or the absence of a carboxyl protecting group, with sulfur trioxide-pyridine complex whereby a protected peptide amide sulfate ester is obtained;

(2) isolating said protected peptide amide sulfate ester by removing the reaction solvent to obtain a residue and adding to the residue first a solvent selected from the group consisting of methanol, ethanol, butanol and dimethylformamide and then an aqueous solution of a water soluble calcium salt selected from the group consisting of calcium acetate, calcium propionate, calcium chloride, calcium bromide and calcium nitrate whereby a calcium salt of said protected peptide amide sulfate ester is obtained; and (3) removing the amino protecting group and, where the carboxyl group is protected, the carboxyl protecting group, and desalting the resulting non-protected calcium salt.

2. The process according to claim 1, wherein sulfuric acid resulting from unreacted sulfur trioxide-pyridine complex is precipitated and removed in the form of calcium sulfate.

3. The process according to claim 1, wherein Y is the carboxyl protecting group.

4. The process according to claim 1, wherein the amino protecting group is tert-butyloxycarbonyl, benzyloxycarbonyl, or α, α-dimethyl-3,5-dimethoxybenzyloxycarbonyl group.

5. The process according to claim 3, wherein said carboxyl protecting group is tert-butyl or benzyl group.

6. The process according to claim 1, wherein the protected peptide amide of the formula (II) is reacted with the sulfur trioxide-pyridine complex by dissolving said protected peptide amide in an inert solvent, adding to the thus-obtained solution the sulfur trioxide-pyridine complex, and then carrying out the reaction at a low temperature at first and then at room temperature.

7. The process according to claim 1, wherein the protecting group or groups are removed by a treatment with trifluoroacetic acid, trichloroacetic acid, hydrochloric acid-dioxane, formic acid, p-toluene sulfonic acid or glacial acetic acid-mercaptoethane sulfonic acid.

8. The process according to claim 1, wherein the desalting step is conducted by ion-exchange chromatography.

* * * * *